United States Patent [19]

Smolko et al.

[11] Patent Number: 5,032,612

[45] Date of Patent: Jul. 16, 1991

[54] NON-SMOKING AID

[76] Inventors: Milan J. Smolko, 802 Jefferson Ave., Scranton, Pa. 18510; Milan S. Smolko, RD #4, Box 134D, Lake Ariel, Pa. 18436

[21] Appl. No.: 529,149

[22] Filed: May 25, 1990

[51] Int. Cl.$^5$ .................... A61K 7/22; A61K 31/28
[52] U.S. Cl. ................................ 514/495; 424/49; 514/495; 514/813; 514/870
[58] Field of Search .................. 131/270, 329, 359; 424/49, 54; 514/495, 970, 813

[56] References Cited

U.S. PATENT DOCUMENTS

| 4,832,994 | 5/1989 | Fey | 428/48 |
| 4,867,181 | 9/1989 | Smolko | 131/270 |

FOREIGN PATENT DOCUMENTS

| 2262497 | 12/1972 | Denmark | 424/49 |
| 2386307 | 4/1977 | France . | |
| 59-152330 | 8/1984 | Japan | 424/49 |
| 2180156 | 3/1987 | United Kingdom | 424/49 |

Primary Examiner—Frederick E. Waddell
Assistant Examiner—Diane Gardner
Attorney, Agent, or Firm—Kane Dalsimer Sullivan Kurucz Levy Eisele and Richard

[57] ABSTRACT

A mouthwash is disclosed and claimed which comprises silver acetate, ammonium nitrate, and nitric acid which, when present as a residue in the oral cavity, will cause an adverse taste when the user smokes a tobacco product. The bitter taste experience causes the development of an aversion to smoking. The use of other non-toxic silver compounds is also disclosed.

16 Claims, No Drawings

NON-SMOKING AID

BACKGROUND OF THE INVENTION

1. Field of the Invention

The invention relates to mouthwash formulations containing non-toxic silver compounds to aid smokers attempting to quit the smoking habit.

2. Brief Description of the Prior Art

The undesirable effects and habituation of smoking tobacco has caused a desire in cigarette, cigar, and pipe smokers to quit their smoking habit. However, withdrawal from nicotine addiction is difficult and the person quitting the habit ordinarily needs assistance.

Aids have been developed to help the smoker. Some aids decrease anxiety during withdrawal, reducing the desire of the user for nicotine. Other aids cause a physiological distaste for tobacco smoke.

Aids which reduce anxiety during nicotine withdrawal have excellent potential, but they do have their shortcomings. For example, a nicotine containing chewing gum is available to quitting smokers and has been proven effective. However, the gum is contraindicated during pregnancy or if the smoker has heart disease. Nicotine chewing gum causes or aggravates heart palpitations, heart attacks, arterial diseases, hypertension, peptic ulcer, diabetes, hyperthyroidism, esophagitis, sore throat, upset stomach, hiccups, nausea, mouth ulcers and addiction to nicotine in 7–10% of users.

Other anti-smoking aids create a local rather than systemic effect. Fr. Demande 2,386,307 (Michalon) discloses a dentrifice with the property of dissuading a smoker from smoking tobacco. The toothpaste contains silver nitrate as the active ingredient to generate a physiological distaste for tobacco smoking.

In U.S. Pat. No. 4,867,181 a mouthwash is disclosed containing silver nitrate which when gargled or rinsed prior to smoking creates a bitter taste when the user smokes a tobacco product.

German Offenlegungsschrift 2,262,497 to Rosenberg discloses tablets containing 400 mg. of silver acetate. Within one to six hours after ingestion tobacco smokers experienced unpleasant taste from their cigarettes.

SUMMARY OF THE INVENTION

The invention is a mouthwash comprised of a solution containing stabilized silver compounds and ammonium nitrate in an aqueous solution, which also helps sore throat and mouth ulcers. In the preferred embodiment, the silver compound is silver acetate.

It has been learned that the inclusion of ammonium nitrate in the mouthwash solution increases the effectiveness of a silver acetate based anti-smoking mouthwash, as well as in anti-smoking mouthwash formulations containing other silver compounds.

Ammonium nitrate in very small amounts, i.e. 0.0006% to 0.006%, improves the effectiveness of anti-smoking mouthwash formulations with silver compound bases by enhancing the bitter taste after inhaling the smoke of cigarettes, cigars, pipes, etc.

Its presence in the mouthwash enables the use of many nontoxic silver compound in an anti-smoking mouthwash. Ammonium nitrate creates similar effects for compounds other than silver nitrate and silver acetate. That is, a bitter taste is experienced only after inhaling tobacco smoke while remaining inert when smoke is not present. Ammonium nitrate can be combined, for example, with silver acetate, silver benzoate, silver sulfate, silver oxalate, silver lactate, silver citrate, and other silver compounds known to those skilled in the art.

The presence of ammonium nitrate enables one to lower the necessary concentration of silver compounds in the solution up to one half. Instead of a silver compound concentration in the range of 0.1% to 0.01%, the practitioner of this invention can use 0.05% to 0.005% of silver compound with similar effectiveness.

A further benefit of ammonium nitrate is that it increases the solubility of less soluble silver compounds where mildly acidic conditions prevail.

Another important ingredient to the mouthwash is nitric acid. By including nitric acid in a concentration of 0.001% to 0.002%, pH is effectively reduced, thereby preventing precipitation of the silver compound. This improves shelf life and stability of the composition. Benzoic acid serves the same purpose when added in concentrations up to 0.001%.

As disclosed in one of the co-inventor's previous patent for anti-smoking mouthwash, an opaque bottle is necessary for stability of the solution.

DETAILED DESCRIPTION OF THE PREFERRED EMBODIMENT

It is proposed herein that a smoking preventative mouthwash can be prepared which utilizes silver acetate as the active, smoking preventative ingredient. Utilizing silver acetate in a mouthwash solution possesses several advantages over the prior art.

Silver acetate, when combined with cigarette smoke, exhibits a metallic taste suggestive of vinegar which causes the desired adverse stimulation to smoking while not exhibiting the degree of adverse reaction experienced when silver nitrate is the active ingredient. Secondly, delivery of silver acetate in a mouthwash is more appropriate than delivery in tablet form. Only the mouth has to be coated for an effective application. It is unnecessary that the tablet be swallowed, which means that the user must wait for the body to absorb the silver compound and then for sufficient concentration be transferred to oral tissues.

The presence of silver acetate in the oral cavity will cause a bitter taste in the mouth only when tobacco smoke is present in the mouth. In the absence of tobacco smoke, the silver acetate is inert and there will be no bitter taste.

Silver acetate is difficult to maintain in an aqueous mouthwash solution and will precipitate from the solution within a few days. However, through steps described below, the mouthwash of the present invention enjoys a shelf life of at least five months to two years under ambient temperature conditions, thus rendering the mouthwash commercially useful.

The silver acetate is used in the composition of the invention in a smoke aversion proportion, which is within the concentration range of 1:1000 to 1:10,000.

The silver acetate is kept in solution through the combination of three factors. The first is to use distilled water free of ions. The impurities usually found in tap water precipitate small concentrations of the silver compound from solution.

The second procedure is the addition of 0.001 to 0.002% of nitric acid to the solution. The nitric acid will retard the precipitation of the silver compound and is a stabilizer.

The third procedure is to package the mouthwash solution in an opaque container. Light will cause silver to precipitate from the solution.

The silver acetate anti-smoking mouthwash of the invention is very safe. In the concentrations disclosed herein, all of the ingredients are safe topically or if swallowed.

In addition to water, silver acetate, ammonium nitrate and nitric acid, the compositions of the invention may also contain a wide variety of ingredients conventionally found in other mouthwash formulations. Examples are preservatives, sweeteners, and like flavorants, coloring agents, glycerin, benzoic acid and alcohols. A person skilled in the art would recognize other permissible additives.

The compositions of the invention may be used by topical application to the mucosa of the oral cavity, at least five times a day for a minimum of three weeks. Gargling, as referred to below, means any manner of topical application. The preferred method of use for optimum results is set forth below.

For the best results the user should gargle at least five times a day for three weeks. First, gargle immediately upon waking, always before lighting a cigarette. Gargling is recommended after meals or after drinking liquids, as foods and liquids reduce the silver concentration in the mouth. In the evening gargle after dinner and two or three hours later. It is believed that the mouthwash imparts a coating concentration that is effective for two to three hours after gargling.

During the first three days it is mandatory to light up and smoke after every gargling with anti-smoking mouthwash. Inhale the smoke two or three times in order to develop an aversion to smoking.

During the remaining eighteen days continue gargling at least five times a day, but it is not mandatory to puff on a cigarette. The user should not keep any cigarettes on his or her person and should remove all tobacco products from the house and workplace.

It is maximally important, that the user does do not stop, interrupt, or decrease gargling for the entire three weeks.

Gargling longer than three weeks is not recommended. If the user wishes to use anti-smoking mouthwash again, he or she should take a break for three weeks and initiate the program from its beginning.

Although no adverse effects have been observed after incidental swallowing of anti-smoking mouthwash, its internal use is not recommended.

The following example sets forth the manner and the use of the invention and sets forth the best mode contemplated by the inventor for carrying out the invention.

EXAMPLE

The following ingredients are mixed together and bottled in opaque bottles, preferably of dark brown plastic.

| | Weight Percent |
|---|---|
| Alcohol (ethanol) | 10% |
| Glycerine | 5.0% |
| Sodium saccharine | 0.002% |
| Silver acetate | 0.05% |
| Nitric acid | 0.001% |
| Ammonium nitrate | 0.003% |
| Pure peppermint abstract | 2-3 drops |
| FD & C Blue #1 | 1 drop |

-continued

| | Weight Percent |
|---|---|
| FD & C Yellow #5 | 1 drop |
| Distilled water to 1000 ml. | |

The mouthwash is stable for at least 5 months retained in the opaque bottles and stored at ambient temperatures (approximately 26° C.).

When used in accordance with the abovedescribed directions, about one-half of smokers develop an aversion to smoking and are able to resist the smoking habit.

As previously noted, a wide variety of embodiments are possible. Other silver compounds are suitable for use as the smoking aversion creating component. The person skilled in the art would not encounter difficulty in substituting any of the aforementioned silver compounds for silver acetate.

What is claimed is:

1. A shelf-stable air for reducing the smoking habit, which comprises a distilled water solution of silver acetate having a concentration within the range of from 1:1000 to 1:10000, stabilized with the presence of 0.001 to 0.00% weight percent of nitric acid, and ammonium nitrate in the concentration of 0.006% to 0.006%, and said aid being protected from exposure to light.

2. The aid of claim 1 wherein the solution additionally comprises basic components of a mouthwash.

3. The aid of claim 1 wherein the solution additionally comprises a flavorant and coloring.

4. The aid of claim 1 wherein the aid is protected from light by storing of the solution in a brown bottle.

5. A shelf stable aid in the form of a solution for reducing the smoking habit, said solution being comprised of distilled water, silver compound selected from the group consisting of silver acetate, silver benzoate, silver sulfate, silver oxalate, silver lactate and silver citrate or any non-toxic silver compound, said silver compound having a concentration in the range of 0.005% to 0.1%, said silver concentration being stabilized in the presence of nitrate acid in a concentration of 0.01% to 0.002% and ammonium nitrate in a concentrate of 0.0006% to 0.006% and said solution being protected from the exposure to light.

6. A shelf-stable aid for reducing the smoking habit, which comprises a distilled water solution of silver acetate having a concentration within the range of from 1:1000 to 1:10000, stabilized with the presence of up to 0.001 weight percent of benzoic acid and ammonium nitrate in a concentration of 0.0006% to 0.006%, and said aid being protected from exposure to light.

7. The aid of claim 6 wherein the aid is protected from light by storing of the solution in an opaque bottle.

8. A composition, which comprises; by weight
10 percent of ethanol;
5.0 percent of glycerine;
0.002 percent of sodium saccharine;
0.05 percent of silver acetate;
0.001 percent of nitric acid;
0.003 percent of ammonium nitrate;
3 drips of peppermint extract;
1 drip FD & C Blue #1;
1 drop FD & C Yellow #5;
the remainder being distilled water.

9. A method of aiding in the reduction the tobacco smoking habit in a human afflicted with said habit, which comprises providing a distilled water solution of silver acetate having a concentration within the range of from 1:1000 to 1:10000, stabilized by the presence of 0.001 to 0.005 weight percent of nitric acid and ammonium nitrate in a concentration of 0.0006% to 0.006% and applying said solution topically to the mucosa of the oral cavity of said human, five times a day, for a period of three weeks and introducing tobacco smoke into the oral cavity following each of the five applications, for the first three days of said three week period.

10. The method of claim 9 wherein the solution is applied by gargling.

11. The method of claim 9 wherein application occurs following a meal or drinking a liquid.

12. The method of claim 9 wherein introducing smoke comprises two to three inhalations of tobacco smoke.

13. A method of aiding in the reduction the tobacco smoking habit in a human afflicted with said habit, which comprises providing a distilled water solution of silver acetate having a concentration within the range of from 1:1000 to 1:10000, stabilized by the presence of up to 0.001 weight percent of benzoic acid and a concentration of 0.0006% to 0.006% ammonium nitrate, and applying said solution topically to the mucosa of the oral cavity of said human five times a day, for a period of about three weeks and introducing tobaco smoke into the oral cavity following each of the five applications, for the first three days of said three week period.

14. The method of claim 13 wherein the solution is applied by gargling.

15. The method of claim 13 wherein application occurs following a meal or drinking a liquid.

16. The method of claim 13 wherein introducing smoke comprises two to three inhalations of tobacco smoke.

* * * * *